United States Patent
Lyon et al.

(10) Patent No.: US 8,269,629 B2
(45) Date of Patent: Sep. 18, 2012

(54) METHOD AND SYSTEM FOR ITEM TRACKING WITH TAGS

(75) Inventors: Geoff Lyon, Menlo Park, CA (US); Salil Pradhan, Santa Clara, CA (US); Bill Serra, Montara, CA (US); Allpio Caban, Arecibo, PR (US); Jorge E Badillo, Rincon, PR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1459 days.

(21) Appl. No.: 11/284,494

(22) Filed: Nov. 21, 2005

(65) Prior Publication Data
US 2007/0115125 A1    May 24, 2007

(51) Int. Cl.
*G08B 13/14* (2006.01)
(52) U.S. Cl. ..................... 340/572.1; 235/385
(58) Field of Classification Search .... 340/572.1–572.9; 235/375–385
See application file for complete search history.

(56) References Cited

U.S. PATENT DOCUMENTS

| | | | |
|---|---|---|---|
| 5,845,264 A | 12/1998 | Nelhaus | |
| 5,892,441 A | 4/1999 | Woolley et al. | |
| 6,697,812 B1 | 2/2004 | Martin | |
| 7,180,421 B2 * | 2/2007 | Pahlaven et al. | 340/572.1 |
| 7,366,675 B1 | 4/2008 | Walker et al. | |
| 7,940,716 B2 * | 5/2011 | Twitchell, Jr. | 370/328 |
| 2005/0275531 A1 * | 12/2005 | Johnson | 340/539.22 |
| 2007/0164863 A1 * | 7/2007 | Himberger et al. | 340/572.1 |

FOREIGN PATENT DOCUMENTS

| | | |
|---|---|---|
| WO | 02/082395 | 10/2002 |
| WO | WO 2004/102330 | * 11/2004 |
| WO | WO2004/102330 | 11/2004 |
| WO | WO 2004102330 A2 | * 11/2004 |
| WO | WO2005/008575 | 1/2005 |

* cited by examiner

*Primary Examiner* — George Bugg
*Assistant Examiner* — Edny Labbees

(57) ABSTRACT

Aspects of the present invention describe a method of tracking an item, comprising. The items is associated with a tag and capable of responding to a query from a tag reader and tag combination. The tag reader and tag combination capable of identifying the item associated with the tag using a tag reader. In operation, a tag reader makes a request to at least one tag reader and tag combination for the identity of an item associated with a tag. The tag reader and tag combination identifies the item associated with the tag and provides the identity of the item and tag to the tag reader.

29 Claims, 7 Drawing Sheets

METHOD AND SYSTEM FOR ITEM TRACKING WITH TAGS

BACKGROUND OF THE INVENTION

Many different items manufactured around the world are shipped in small and large cargo containers. These cargo containers often contain hundreds and thousands of items in packages and a variety of smaller boxes and containers. In some cases, the cargo containers are moved directly between ships at port while in other cases they may travel over land on trains and trucks to then be reloaded on ships or other transportation. Many of the items shipped in this manner arrive at their destination as planned and the shipping is considered successful.

Unfortunately, there are also times that items to be shipped do not make it to their destination as planned. In some cases, the items meant to be packed in a container are never actually loaded. If this occurs, the recipient of a shipment may not even discover the items are missing until after the inventory has been received and the items counted. Further, it is also possible that containers may be vandalized and certain items stolen or even replaced with inferior goods or knock-offs. In either of these scenarios, it helps to quickly determine when items have been stolen or swapped as missing items or knock-offs may go undetected for days or years.

Given the enormous quantities of items being shipped and transported, accurately detecting and tracking items is difficult if not impossible. Hundreds and thousands of items in large standardized shipping containers would be delayed several days or weeks in each port as items are inventoried using manual or even semi-automatic inventory methods and equipment. Alternatively, estimating the number of items contained in boxes, pallets or shipping container is faster but the results are also not acceptable given the inaccuracies and potential lost revenues from making such estimations. Accordingly, the costs, delay and inaccuracies associated with any of the current approaches for tracking and inventorying items remains unacceptable.

BRIEF DESCRIPTION OF THE DRAWINGS

Like reference numbers and designations in the various drawings indicate like elements.

SUMMARY OF THE INVENTION

Figure 1:
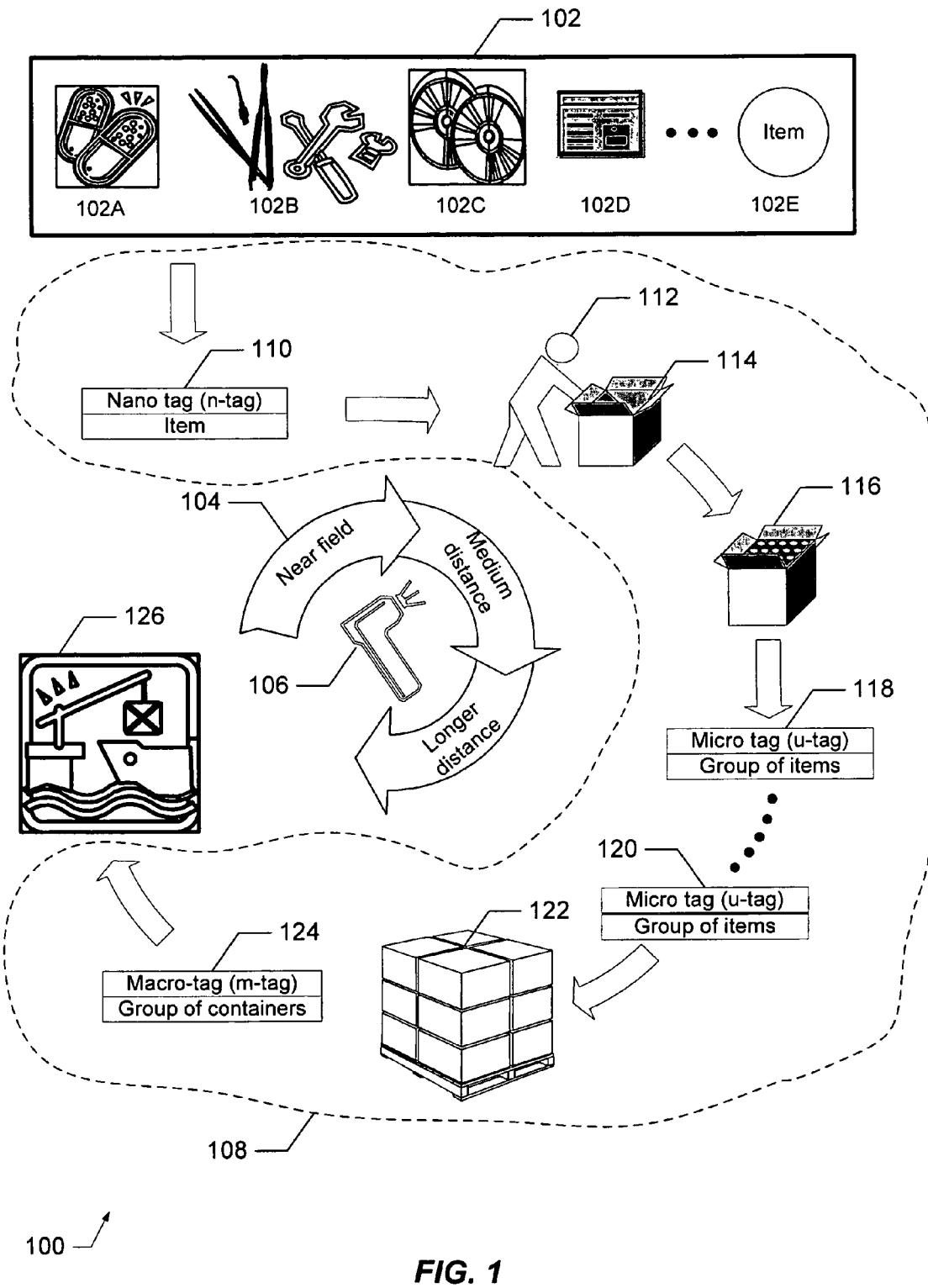
FIG. 1 is a schematic diagram of a system for tracking an item passing through an item distribution network.

One aspect of the present invention features an apparatus used when tracking an item. The item is associated with a tag and capable of responding to a query from a tag reader and tag combination. The tag reader and tag combination identifies the item associated with the tag using a tag reader. This information is passed up from the tag reader and tag combination to a tag reader.

Another aspect of the present invention includes a method of tracking the item. A tag reader makes a request to at least one tag reader and tag combination for the identity of an item associated with a tag. The tag reader and tag combination identifies the item associated with the tag and provides the identity of the item and tag to the tag reader.

DETAILED DESCRIPTION

Implementations of the present invention accurately and quickly track and account for a large number of items. A hierarchy of tag reader and tag combinations is used to organize and identify items in one or several containers. Tags at different levels in the hierarchy can be detected over different distances using depending on the strength of the radio frequency identification (RFID) tag.

At the lowest level of the hierarchy, each item is associated with a near field tag having a range covering a nearby range or field. The items associated with the near field tags are detected by an intermediary set of tags also having near field tag readers. These intermediary set of tags are detectable over a wider intermediate range or field greater than that of the near field tags. The intermediate set of tags can also communicate with each other providing an aggregate list of the items and their corresponding identifiers. Generally, near field tags are designed to operate over a specific area or range and then drop off sharply beyond the specified distance. Expected distances between a reader and the tag or tags being targeted may influence the power requirements for a tag and the contour of the signal propagated between tag and reader. Depending on the number of items and how they are packaged, multiple layers of tags can be added to the hierarchy of tags to accommodate the particular configuration.

Aspects of the present invention are advantageous in at least one or more of the following ways. An accurate count and inventory of items can be done from a tag reader at a single point rather than requiring a scanning of each and every item. It is possible for a single tag reader to obtain an accurate count and inventory of the items with a single reading of a tag because the information associated with near field tags is passed up through the hierarchy of tags. Each request made at a tag reader and tag combination causes each downstream tag in the hierarchy of tags to gather up tag information on multiple groups of items. Once again, the results are returned through the hierarchy to the tag reader that initiated the request. A large number of items can be counted accurately in this manner without damaging the goods or requiring extensive delay.

Additionally, implementations of the present invention reduce the likelihood of tampering or losing items in transit. Items placed in a standardized cargo container or storage device can be accounted for each time the container is shipped, moved or transferred between carriers. For added security, a reader device can even request status on a more frequent basis to track the status of items in transit. If items are lost or destroyed due to weather or other causes, the missing items would be detected almost immediately. Many other benefits and advantages are also possible and contemplated in view of the figures, description and claims provided herein.

FIG. 1 is a schematic diagram of a system 100 for tracking an item passing through an item distribution network. In this illustrated example, system 100 includes items from a manufacturer 102, a tracking sequence 104, a tag reader 106, a packing sequence 108 and a carrier 126. In this context, manufacturer 102 can be a business involved in the actual creation or manufacture of the product or item as well as any business that packages existing items and redistributes them in accordance with aspects of the present invention. Likewise, the term 'end user' is a descriptive term selected for convenience and includes any company, business, fictitious, or real person that tracks an item along tracking sequence 104 using a tag reader 106. For example, an end user 112 can represent a shipping company tracking a shipment of drugs from manufacturer 102 or can represent a drug distributor tracking a package of drugs passing through any point along packing sequence 108. In general, end user 112 can also include any carrier that tracks an item along packing sequence 108 and desires to inventory the item in accordance with implementations of the present invention. As will be described in further detail below, tag reader 106 represents different types of readers including a near field tag reader, a medium distance tag reader or a longer distance tag reader; each capable of reading tags at different distances. Tag reader 106 generally is compatible with RFID tag technologies however alternate implementations are contemplated to work with bar-code or other inventory systems in accordance with various alternate implementations of the present invention.

In this example, manufacturer 102 manufactures, creates and/or repackages various items including drugs 102A, tools 102B, media 102C, devices 102D and any other item 102E. Drugs 102A can be delivered through pills, elixirs, inhalers, injectable materials, transdermal patches, subcutaneous drug implants or any other delivery mechanism. Tools 102B include medical tools, automotive tools and any other tools while media 102C represents various storage devices used to hold media including compact discs (CD), digital video discs (DVD), flash memory and the electronics equipment associated with processing media stored on these media 102C. Devices 102D include smaller electronic and mechanical devices, medical devices, as well as more complex items like computers and data storage systems. While only a few classes of items are illustrated for brevity, manufacturer 102 can be involved with any other item 102E susceptible to loss, counterfeiting, identification or tracking using a tag. For example, this could also include automobiles, sporting equipment, luxury items (i.e., purses, handbags, shoes, leather goods) and many other items as it is contemplated that aspects of the present invention could be widely used in many different industries and businesses.

In one implementation, manufacturer 102 associates a nano-tag (n-tag) 110 with each item using RFID, barcode or other technologies. To make the tracking with system 100 cost effective, nano-tag 110 can be made low in cost and disposable. Nano-tag 110 can be integrated into a conventional box, a medicine vial, shrink wrap, plastic material or other packaging material; alternatively, nano-tag 110 could be integral to the item. For example, nano-tag 110 could be an RFID tag embedded within or on the surface of drug 102A making drug 102A both the item being tracked as well as encompassing nano-tag 110. A nano-tag 110 can also be permanently or semi-permanently attached to items 102A-E during manufacture or shortly thereafter using adhesive or mechanical methods (i.e., rivets, staples, prongs). In any event, nano-tag 110 is associated with each item to be tracked either by placing the item in a package having nano-tag 110 or by integrating nano-tag 110 directly into or onto the item.

In the hierarchy, nano-tag 110 is detectable over the shortest distance or range in accordance with the present invention. For example, nano-tag 110 can represent a near field tag associated with an item and capable of being detected by a near field tag reader. Using a passive RFID, the near field tag reader may need to be 1-2 mm in distance from the near field tag to properly identify it.

An identifier associated with each nano-tag 110 is read by a near field tag type of reader 106 and used to identify the item. As will be described later herein, nano-tag 110 is a label indicating that it is the first tag in a hierarchy of tags capable of being read at different distances. Accordingly, while nano-tag 110 may be described in terms of being a near field tag it is contemplated that nano-tag 110 is not limited to being detected at a distance of 1-2 mm or any other particular distance as long as it fits within a hierarchy of tags and tag readers operating over different ranges.

In this example, each nano-tag 110 and item are tracked and then packaged into a container 114 by an end user 112. As previously described, end user 112 is not necessarily a person and can be a company or other entity. End user 112 places nano-tag 110 and item into container 114 in a manner that facilitates subsequent readings using a near field type of tag reader 106. If it is appropriate, container 114 can be a box for holding multiple nano-tags and items in the form of a blister pack for holding pills or other items, as described later herein.

Full container 116 includes a micro-tag 118 capable of detecting nano-tag 110 and associated items placed in container. In particular, micro-tag 118 is attached to or integrated into container 114 and has a near field reader positioned to read each nano-tag 110 from each item. In addition to the near field reader, micro-tag 118 also has a tag capable of being detected over an intermediate range or field useful when transmitting information about the one or more nano-tag 110 and items in the vicinity of the micro-tag. Additional containers are tracked using an additional one or more micro-tag 120.

A group of containers 122 are tracked by a macro-tag 124. In one implementation, each full container 116 in group of containers 122 has at least one more micro-tag keeping track of the individual nano-tag 110 and associated items. Macro-tag 124 is another tag reader and tag combination capable of reading micro-tag 118 through micro-tag 120 and receiving the identification information for micro-tag 118 through micro-tag 120 as well as nano-tag 110 and corresponding items.

In one implementation, each micro-tag 118 through 120 has a passive RFID tag combined with a near field reader and is disposable or very low in cost. Macro-tag 124 combines a passive RFID reader with an active RFID tag and can be reused if it is desired or cost-effective. Typically, macro-tag 124 has an even greater range or field than micro-tag 118 through 120 or nano-tag 110. Further, macro-tag 124 is capable of communicating with other macro-tags by forming a daisy chain or cascade-like network of RFID devices. An end user 112 on carrier 126 can query one macro-tag 124 to obtain information about other macro-tags, micro-tags, groups of containers and ultimately each item and nano-tag 110 being transported or received.

Figure 2A:
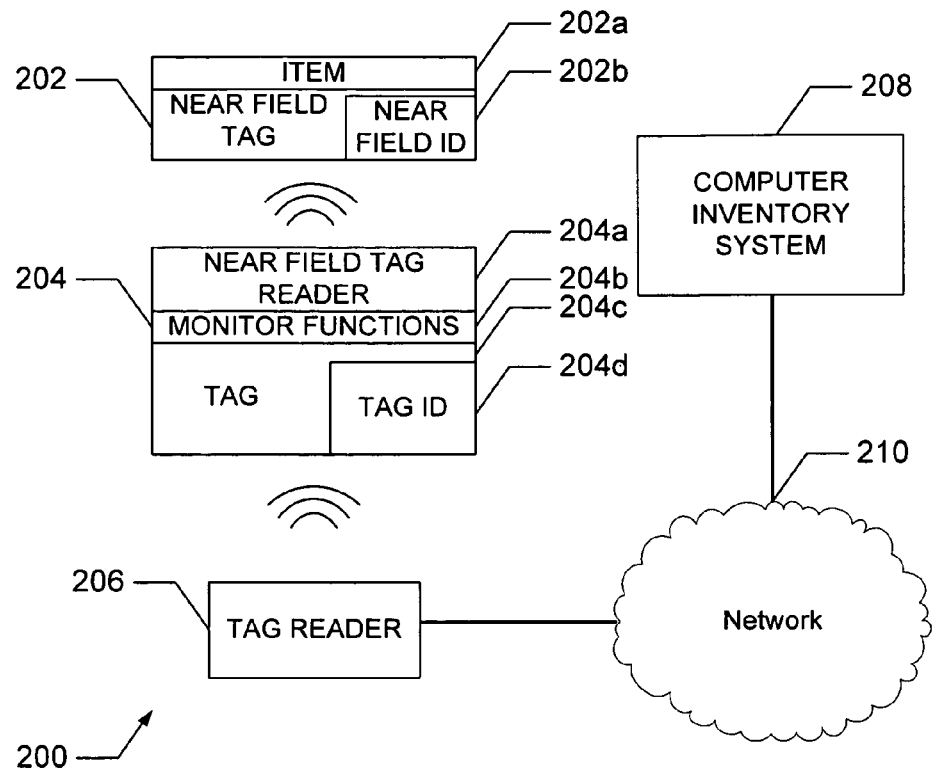
FIG. 2A is a schematic diagram depicting a hierarchical relationship between one or more tag reader and tag combinations in accordance with one implementation of the present invention.

FIG. 2A is a schematic diagram depicting a hierarchical relationship between one or more tag reader and tag combinations in accordance with one implementation of the present invention. At the lowest level of the hierarchy in FIG. 2A, a near field tag 202 includes a near field id 202*b* and is associated with an item 202a. Compared with other tags, near field tag 202 is detectable over a smaller range or distance. Near field tag 202 is generally designed as a passive tag to keep costs especially low and allow the tags to be disposed of if necessary. With respect to FIG. 1, near field tag 202 can be classified as one type of nano-tag as described previously.

Next in the hierarchy is a near field tag reader and tag combination 204 (combination tag 204) including a near field tag reader 204a, monitor functions 204b, a tag 204c and a tag id 204d. Near field tag reader 204a is placed in close proximity to near field tag 202 to enable it to read and write data to near field tag 202. Monitor functions 204c gathers ambient and other information to be associated with data from near field tag 202. For example, ambient information can include temperature, pressure, vibration, gas composition or any other information measurable by a sensor. This ambient information from monitor functions 204b can be useful if item 202a needs to be in a controlled environment with specific limitations on temperature, pressure, vibration, certain gases and/or other environmental constraints. The information gathered from near field tag reader 204a and monitor functions 204b is transmitted up the hierarchy through tag 204c for subsequent data collection and analysis. Typically, tag 204c is detectable over a greater range or distance compared with the near field tag 202 described previously and is an active tag having its own source of power. Of course, tag 204c could also be a passive tag as dictated by the particular overall system design.

Tag reader 206 communicates with combination tag 204 to discover information regarding item 202a. Alternatively, tag reader 206 can also communicate with other near field tag reader and tag combinations (not shown). In operation, near field tag 202 associated with item 202a responds to queries from combination tag 204. Typically, combination tag 204 is positioned close enough to near field tag 202 to identify item 202a associated with near field tag 202. Item 202a can be a drug, medical device, computer equipment, luxury item, sports equipment or any other item suitable for tracking. Tag identification and other information associated with item 202a can be passed through near field tag 202, combination tag 204, tag reader 206 and network 210 onto computer inventory system 208. This information can be collected on an occasional basis or more frequently to keep track of item 202a continuously or in real-time.

FIG. 2A also depicts other operational aspects the hierarchical combination of a tag reader 206, combination tag 204 and near field tag 202. The top-most tag reader 206 generates a mid-range RF field to interrogate combination tag 204. Combination tag 204 also contains embedded reader functionality so that it can, in-turn, generate a shorter range RF field of its own and interrogate the lower-level near field tag 202.

Combination tag 204 contains the functionality of a generic RFID tag (e.g. an energy collection and conditioning circuit, a clock extraction circuit, a state machine driven "brain" or control logic, a unique ID value and a modifiable read-write memory block for user data storage). In addition, combination tag 204 also contains additional circuitry so it can function as tag reader 204a (e.g. an internal frequency source circuit, an antenna driver circuit and RF demodulation circuitry). This additional circuitry allows combination tag 204 to re-propagate some of the energy it receives and power, send and receive data from near field tag 202, positioned lower in the hierarchy. In a low cost implementation, all of the combination tag 204 circuitry (with the exception of the antenna structures) would be built into a single integrated circuit.

During operation, the antenna on combination tag 204 receives RF energy from the RF field generated by tag reader 206. This energy becomes an electrical signal circulating through the tag's antenna, which is converted into a steady DC signal by a rectification circuit. This provides a stable source to power combination tag's 204 internal circuitry. Some of this energy is used to power tag 204c functionality, enabling tag 204c to back-propagate information (such as the tag ID) to the tag reader 206. The remaining energy is used to power near field tag reader 204a reader functionality. This creates a secondary short-range RF field to power the lower-level near field tag 202.

In a typical RFID implementation, the operating RF frequency is fixed within specific spectral bands, often limited by FCC regulations. In the case of a hierarchical scheme as shown, it maybe beneficial to operate the different RF links using differing frequency allocations to avoid inter-link interference. In certain cases, the ISM (industrial scientific and medical) frequency allocations are direct multiples of each other, therefore the higher-level clock signal extracted by combination tag 204 could be halved (using a single latch gate) to generate the RF frequency reference for the lower-level link. Alternatively an internal PLL circuit could be used to create the secondary frequency by combination tag 204. In any case, one design goal would be to achieve this functionality with the minimum of power consumption. It is contemplated in an ideal implementation that all of the energy captured by combination tag 204 would be used to generate the RF field for the lower-level link, thus maximizing the range of the lower-level near field tag 202 being read. In a more practical and realistic sense, some portion of the energy imparted to combination tag 204 will not be transmitted to near field tag 202 as the energy will be consumed to power the combination tag's 204 internal circuitry.

Figure 2B:
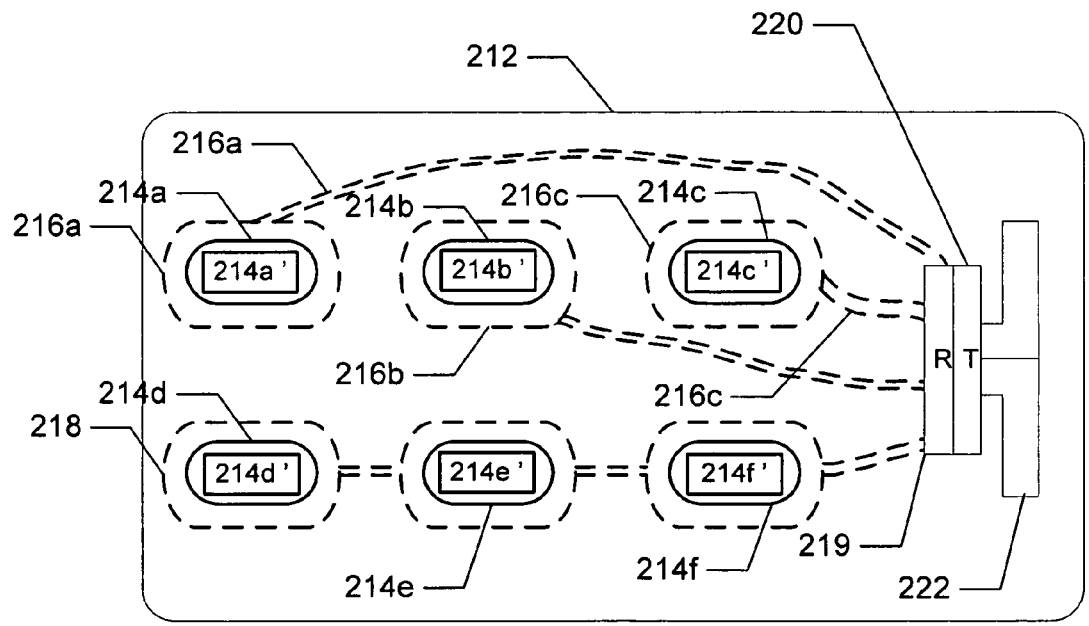
FIG. 2B is one example implementation of the present invention for packaging and tracking pharmaceuticals.

In FIG. 2B is one example implementation of the present invention for packaging and tracking pharmaceuticals. As it is depicted, a tracking apparatus for pills is manufactured as a bubble pack 212 capable of holding a set of pills 214 a-f and having near field antennas 216a-c and antenna 218 near a holding area for each pill in set of pills 214a-f. Bubble pack 212 further includes a near field reader 219 to identify one or more near field tags 214a'-f' associated with each pill in set of pills 214a-f. When energized, tag 220 and tag antenna 222 transmit information about set of pills 214a-f to a more distant positioned tag reader (not shown). If tag 220 is implemented as an active tag then it does not need to be energized and will send information to be read by any tag reader in the vicinity until it loses its charge or runs down any internal batteries or power source.

In one implementation as depicted, near field antennas 216a-c surround holding areas for each pill and are each directly coupled to near field reader 219. In certain circumstances, this arrangement ensures that even the smallest near field tags 214a'-c' associated with pills 214a-c can be detected and read/written. Alternatively, parts of antenna 218 surround different holding areas for each pill but are coupled together in series and then connected near field tag reader 219. This arrangement allows for denser and lower cost packaging as only a single antenna connection is required to near field tag reader 219 rather than multiple connection points. By carefully designing bubble pack 212 and antenna 218, small near field tags 214d'-f' and associated pills 214d-f can also be detected reliably by near field reader 219. Both types of antenna connections (i.e., direct and in series) are depicted in FIG. 2B for illustration, however in practice a single bubble pack 212 is more likely to adopt either a direct (i.e., antennas 216a-216c) or series type antenna (i.e., antenna 218) configuration rather than both or multiple types of antenna configurations.

As previously mentioned, items such as pills can be surrounded with a container having an identifier or the identifier can be embedded within the item. For example, one or more pills can be placed in a blister pack or vial having an RFID, a bar code, an alphanumeric identifier imprinted on the package. Each pill could also be individually identified by embedding each pill with an RFID tag and identifier or imprinting the barcode or alphanumeric identifier thereupon. In addition to drugs, implementations of the present invention could be applied to many other items including: medical devices, computer equipment, electronics, luxury items, sports equipment or any other item susceptible to being identified and tracked.

Figure 3:
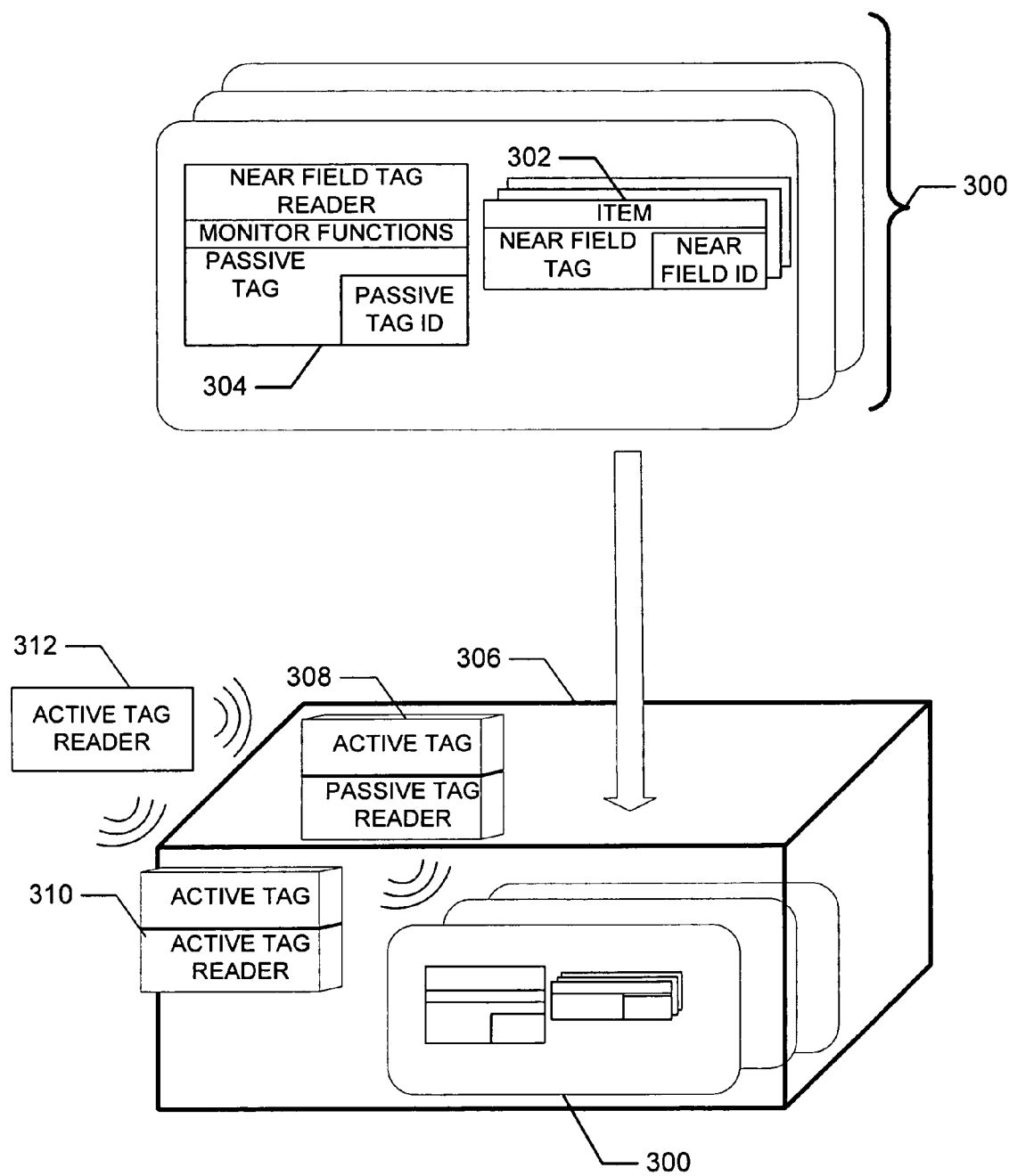
FIG. 3 is a schematic for packaging and tracking multiple items in accordance with one implementation of the present invention.

Referring to FIG. 3, a schematic illustrates packaging and tracking multiple items in accordance with one implementation of the present invention. In this example, contents 300 include multiple sets of items 302 and corresponding near field tag reader and tag combinations 304. For example, each set of items and corresponding near field tag reader and tag combination can correspond to one blister pack of pills as previously described. Alternatively, the set of items could be any other item to be identified and tracked other than pills. Contents 300 are placed within a container 306 and these containers are stacked on palettes and/or placed in even larger standardized containers for shipping on a common carrier.

In one implementation, container 306 has a passive tag reader and active tag combination 308 and an active tag reader and active tag combination 310 attached to different points of container 306. When inventory is to be taken, an active tag reader 312 is positioned in the proximity of container 306 to interact with either or both passive tag reader and active tag combination 308 and/or active tag reader and active tag combination 310. In one mode of operation, active tag reader 312 queries passive tag reader and active tag combination 308 to obtain detailed information on contents 300. The passive tag reader portion energizes and queries near field tag reader and tag combination 304 as well as multiple sets of items 302. This causes near field tags associated with the various items in contents 300 to provide one or more near field id thus identifying the various items. Identification information is provided up the hierarchy to active tag reader 312 initiating the request.

In an alternate mode of operation, active tag reader 312 queries active tag reader and active tag combination 308 to obtain detailed information on other containers (not shown) and their respective contents. Active tag reader and active tag combination 310 operates as a proxy for active tag reader 312 and queries other containers forming a cascade-like network of containers and their contents. For example, active tag reader and active tag combination 310 passes a request to passive tag reader and active tag combination 308 to query for contents 300. In turn, the passive tag reader portion of passive tag reader and active tag combination 308 energizes and queries near field reader and tag combinations 304 as well as multiple sets of items 302. Once again, this causes near field tags associated with the various items in contents 300 to provide one or more near field id thus identifying the various items. Contents 300 within each container in the cascade-like network of containers provides identification information up the hierarchy of tag reader and tag combinations to active tag reader 312 initiating the request.

Figure 4:
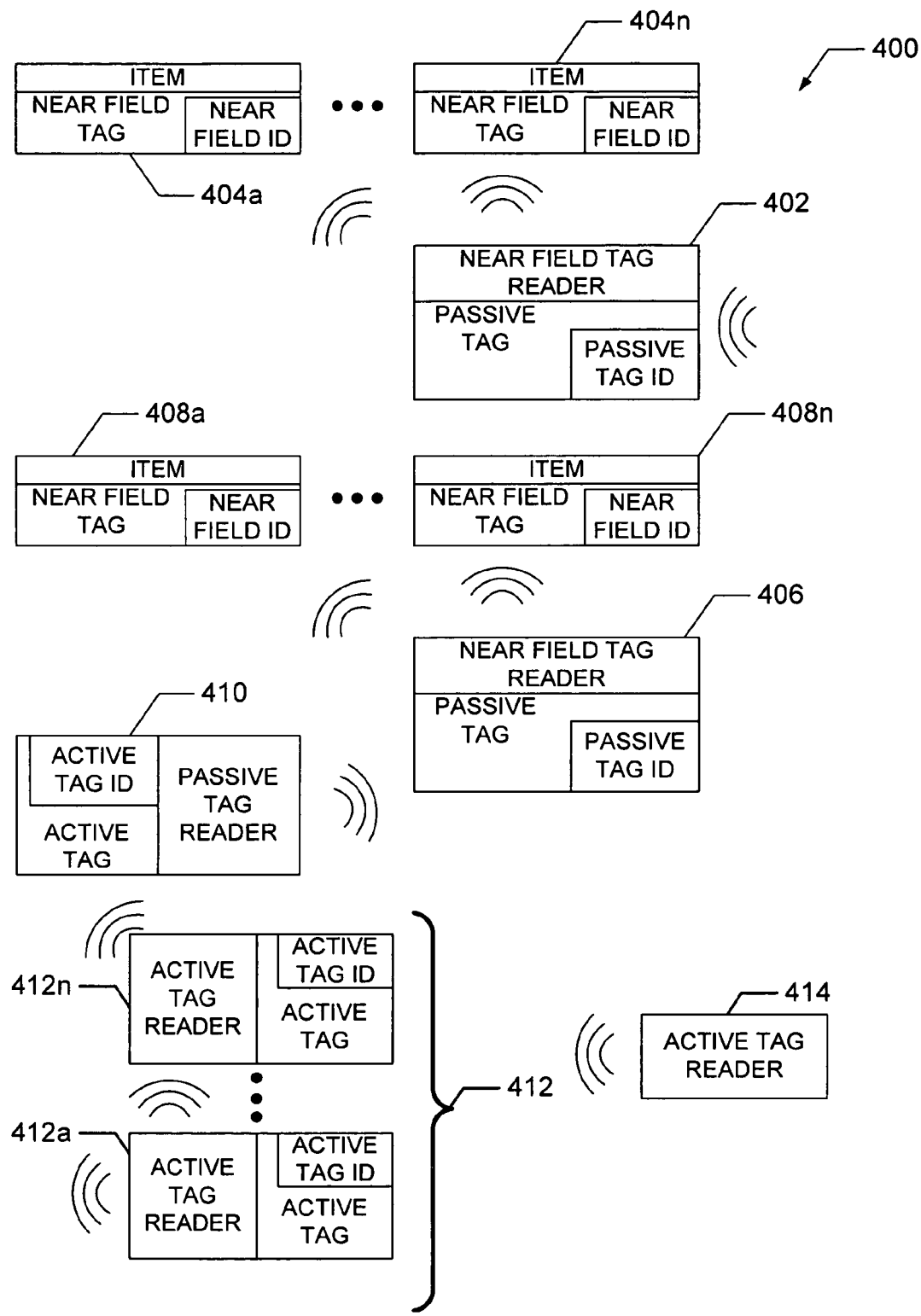
FIG. 4 schematically depicts a cascading request for items using a series of active tag reader and active tag combinations according to one implementation of the present invention.

FIG. 4 schematically depicts a cascading request for items using a series of active tag reader and active tag combinations 412 in an inventory system 400 according to one implementation of the present invention. Computer inventory systems and other networking details are contemplated but omitted for clarity.

In this example, an active reader 414 is located remotely and provides a query to a series of active tag reader and active tag combinations 412 for items 404a through 404n and 408a through 408n for status and tracking purposes. The query travels from active tag reader and active tag combination 412a to active tag reader and active tag combination 412n in a manner as previously described until it reaches passive tag reader and active tag 410 which is located more closely to items 404a through 404n and 408a through 408n.

For example, active tag reader 414 can energize the sequence of active tag reader and active tag combination 412a through active tag reader and active tag combination 412n. The sequence of the active tag reader and active tag combinations generally are configured in a daisy-chain pattern that connects a tag reader portion to a tag portion of a subsequent combination. This allows a request to propagate through an arbitrary number of containers associated with these tags and travel over a substantial distance. Eventually, an active tag reader and active tag combination energizes the circuitry in a passive tag reader and tag element in inventory system 400.

In response, the passive tag reader portion of passive tag reader and active tag combination 410 energizes and queries near field tag reader and tag combinations 402 and 406 as well as items 404a through 404n and 408a through 408n. The near field tags associated with these items provides one or more near field id thus identifying the requested items located at some distance to active tag reader 414. This example illustrates the ability for a remotely located active tag reader 414 to accurately and efficiently track items 404a through 404n and 408a through 408n located an arbitrary distance away.

Figure 5:
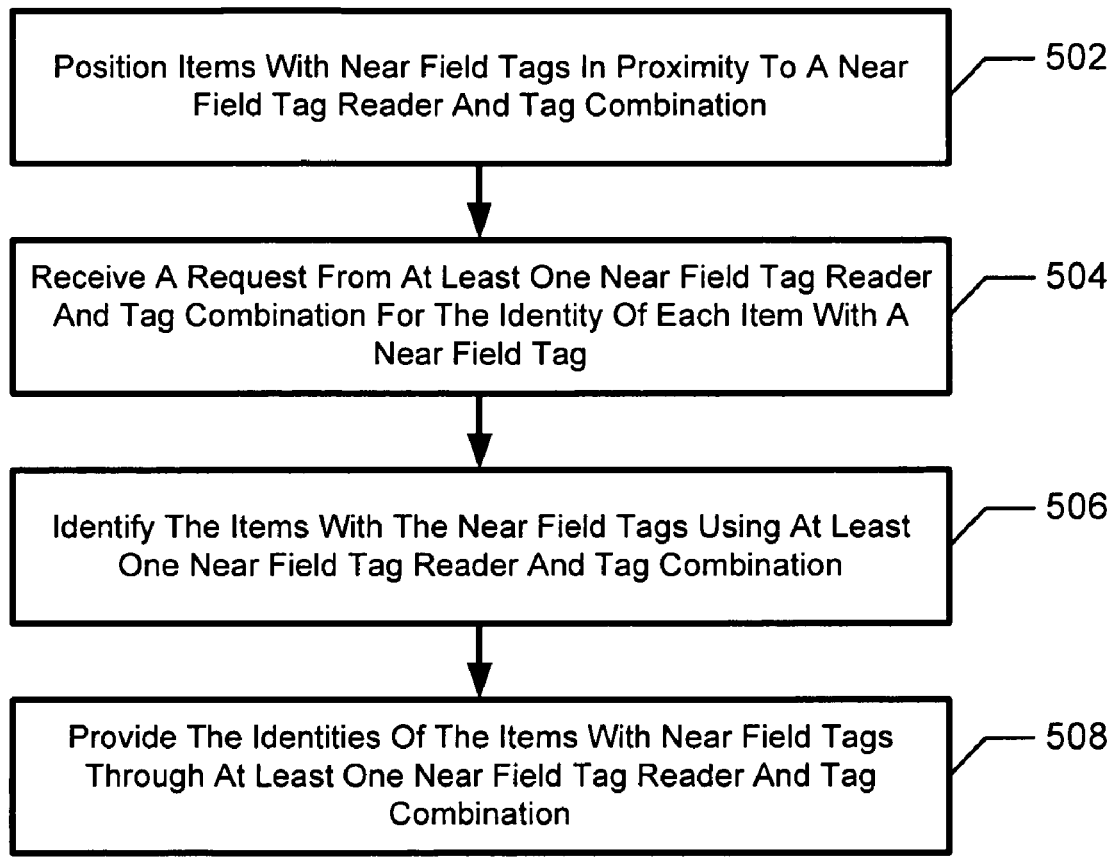
FIG. 5 is a flowchart diagram of the operations for tracking an item in accordance with one implementation of the present invention.

FIG. 5 is a flowchart diagram of the operations for tracking an item in accordance with one implementation of the present invention. Initially, a user or machine position items with near field tags in proximity to a near field tag reader and tag combination (502). For example, a set of pills can be inserted into the respective holding areas of a blister pack designed in accordance with implementations of the present invention. As previously described, a near field tag can be embedded in each pill or can be attached to the surface of each pill.

Next, a request is received from at least one near field tag reader and tag combination for the identity of each item with a near field tag (504). The request may have been initiated by a local or remotely located reader device performing inventory and tracking of the items. In response, the identities of the items with the near field tags are determined using at least one near field reader tag and tag combination (506). For example, a near field tag reader and tag combination energizes the near field tags associated with various items. In return, the near field reader tag receives near field tag identification information. The system provides the identities of the items through at least one near field tag reader and tag combination (508). One or more near field tag reader and tag combinations can provide the identification information up one or more levels of the hierarchy of tags.

Figure 6:
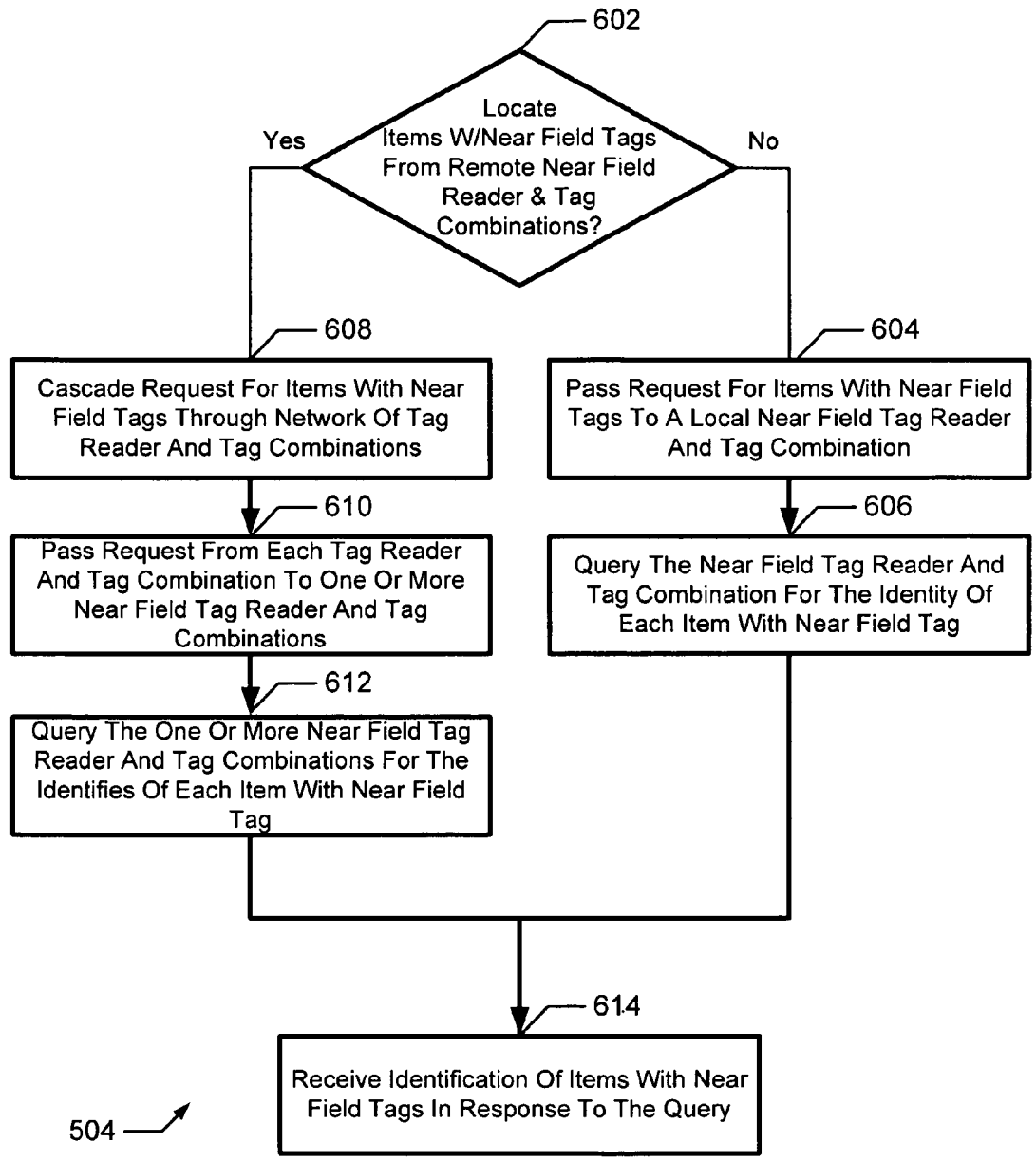
FIG. 6 is a flowchart diagram for obtaining identification information of items located either locally or remotely to a tag reader in accordance with implementations of the present invention.

FIG. 6 is a flowchart diagram for obtaining identification information of items located either locally or remotely to a tag reader in accordance with implementations of the present invention. Receiving a request for identification information can require determining whether the items with near field tags are near a local near field reader and tag combination or associated with one of multiple remote near field reader and tag combinations (602). In the event the items are local then the request is passed to a local near field reader and tag combination (604). For example, the local near field reader and tag combination can be located near the tag reader making the request. A query made to this local near field tag reader and tag combination then provides the identity of each item associated with a near field tag (606) in a manner previously described.

Alternatively, receiving a request for identification information of items located remotely to a tag reader device is more complex. This is because the distance between the near field tag reader and tag combination and associated items is too great for the tag reader to make a direct read. Accordingly, the tag reader device cascades the request for items with near field tags through a series or network of tag reader and tag combinations (608). Each tag reader and tag combination passes the request to one or more near field reader and tag combinations (610) as previously described. Instead of receiving the identification information of a few items, a query to the one or more near field reader and tag combinations in the network provides the identities of each item with a near field tag (612) in the proximity. If it is desired, this could include all the information and identification for all items in inventory rather than just a few items associated with a particular near field reader and tag combination. In either approach described above, the tag reader receives the identification information of one or more items in response to the query (614).

Figure 7:
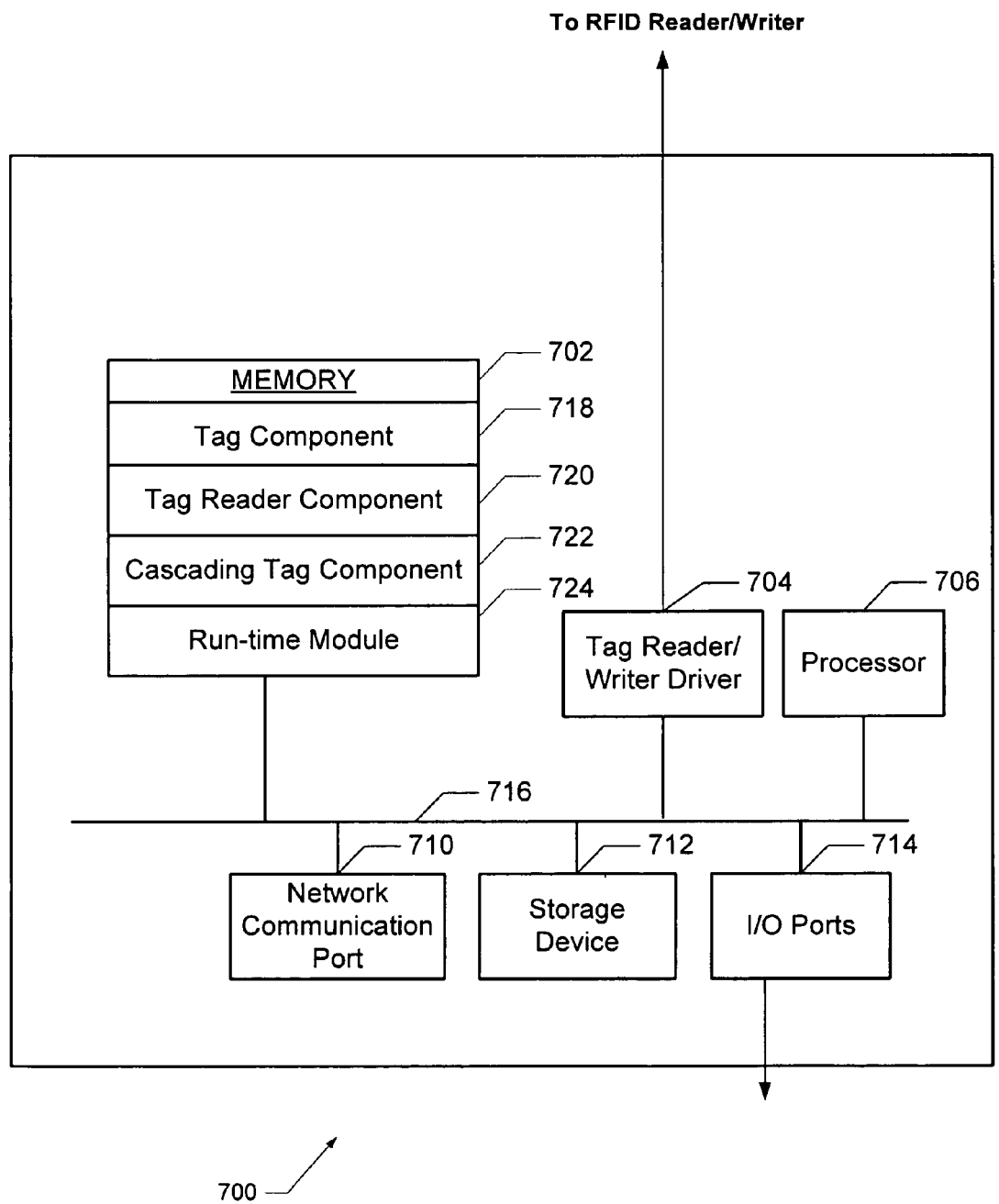
FIG. 7 is a schematic diagram of a tag reader and tag combination and components for tracking items in accordance with one implementation of the present invention.

FIG. 7 is a schematic diagram of a tag reader and tag combination 700 and components for tracking items in accordance with one implementation of the present invention. Combination 700 includes a memory 702 to hold executing components or programs (typically random access memory (RAM) or read-only memory (ROM) such as a flash RAM), a tag reader/writer driver 704, a processor 706, a network communication port 710 for data communication, a storage device 712, and input/output (I/O) ports 714 with integrated I/O controller operatively coupled together over an interconnect 716. Combination 700 can be preprogrammed, in ROM, for example, using field-programmable gate array (FPGA) technology or it can be programmed (and reprogrammed) by loading a program from another source (for example, from a floppy disk, a CD-ROM, or another computer). Also, combination 700 can be implemented using customized application specific integrated circuits (ASICs).

In one implementation, memory 702 includes tag component 718, tag reader component 720, cascading tag component 722 and run-time module 724 that manages the resources associated with combination 700. In operation, tag component 718 processes identification information and passes it up a hierarchy of tag readers in accordance with implementations of the present invention. Further, tag reader component 720 receives requests for identification information from an item and instead passes these requests or queries down the hierarchy of tag readers until the item and identification information is located. Cascading tag component 722 is used when the item may be associated laterally across a cascaded network of tag reader and tag combinations. Accordingly, cascading tag component 722 is responsible for passing a request along laterally to other tag reader and tag combinations to locate a potentially remotely located item and associated identification information. Tag reader/writer driver 704 performs reads and writes on an item and the associated near field tag or regular tag as needed.

While examples and implementations have been described, they should not serve to limit any aspect of the present invention. Accordingly, implementations of the invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs.

While specific embodiments have been described herein for purposes of illustration, various modifications may be made without departing from the spirit and scope of the invention. For example, the term near field is used to distinguish one tag or reader from another tag or reader in a hierarchy of tags and readers. In some cases, near field indicates that the tag or reader covers a smaller area or has a shorter range than other tags or readers. However, it is possible that a tag or reader identified as near field may cover a larger area or have a longer range than others in the hierarchy. Essentially, near term delineates the different tags and readers but should not be construed as limited to one specific distance or signal strength. Further, active and passive tags and tag readers are described and used in different implementations of the present invention however it is contemplated that they can be used interchangeably. The type of active or passive reader or tag depends on the implementation, the power required by each tag while being tracked or tracking other tags, the organization of items and their tags and whether or not some or all of the tags and items are considered disposable or reusable. Accordingly, the invention is not limited to the above-described implementations, but instead is defined by the appended claims in light of their full scope of equivalents.

What is claimed is:
1. A method of tracking an item, comprising:
receiving a request on at least one combination tag reader and tag for the identity of an item associated with a tag;
identifying the item associated with the tag using a tag reader portion of the at least one combination tag reader and tag in a daisy-chain sequence of combination tag reader and tag; and
providing the identity of the item and tag through a tag portion of the at least one combination tag reader and tag.

2. The method of claim 1 wherein the item is selected from a set of items including: drugs, medical devices, computer equipment, luxury items, and sports equipment.

3. The method of claim 1 wherein the at least one combination tag reader and tag receives the request and further receives energy for both the tag reader portion and the tag portion from a reader in a sequence of combination tag reader and tags.

4. The method of claim 1 wherein receiving the request further includes:
   passing the request for the identity of the item associated with the tag to a sequence of at least one or more combination tag reader and tags; and
   querying through the tag reader portion of each of the one or more combination tag reader and tags for the identities of items associated with tags.

5. The method of claim 1 wherein receiving the request further includes:
   cascading the request for the item associated with the tag through a daisy-chain sequence of the at least one or more combination tag reader and tags wherein the cascading further includes,
   passing the request from the tag portion in each combination tag reader and tag through to the tag reader portion and onto a subsequent one or more combination tag reader and tags; and
   querying the daisy-chain sequence of the one or more combination tag reader and tags for the identities of items associated with a tag.

6. The method of claim 1 wherein the tag portion in the combination tag reader and tag is selected from a set of tag types including: a passive tag and an active tag.

7. The method of claim 1 wherein the identity of the item is stored in the tag portion.

8. The method of claim 1 wherein the tag is configured to operate as a near field tag.

9. The method of claim 1 wherein the tag portion of the tag reader and tag combination is configured to operate as a near field tag.

10. A tracking apparatus comprising:
   a tag associated with an item and capable of responding to a query from a combination tag reader and tag; and
   a combination tag reader and tag capable of using the tag reader portion thereof for identifying the item associated with the tag;
   a tag reader capable of querying the tag associated with the last combination tag reader and tag in a daisy-chain sequence of at least one or more combination tag reader and tags for the identity of the item associated with the tag.

11. The apparatus of claim 10 further comprising:
   a computer inventory system capable of receiving from the combination tag reader and tag the identity of the item associated with the tag and holding the identity for later reference.

12. The apparatus of claim 10 wherein the combination tag reader and tag receives a request and receives energy for both the tag reader portion and tag portion from a tag reader in a sequence of combination tag reader and tags and transmits a predetermined amount of the energy to a tag portion on a subsequent combination tag reader and tag.

13. The apparatus of claim 10 wherein the item is selected from a set of items including: drugs, medical devices, computer equipment, luxury items, and sports equipment.

14. The apparatus of claim 10 wherein the tag portion in the combination tag reader and lag is selected from a set of tag types including: a passive tag and an active tag.

15. A tracking apparatus for pills comprising:
   a bubble pack capable of holding a set of pills and having at least one antenna near a holding area for each pill in the set of pills; and
   a combination tag reader and tag integrated into the bubble pack, wherein the tag reader portion of the combination tag reader and tag is operatively coupled to the at least one antenna near the holding area for each pill to facilitate identification of a tag associated with each of the one or more pills in the set of pills to be placed in their respective holding area.

16. The apparatus of claim 15 further comprising:
   a set of pills in the holding area wherein at least one pill is associated with a tag capable of responding to a query from the combination tag reader and tag.

17. The apparatus of claim 15 wherein the at least one antenna near the holding area is operatively coupled to the tag reader portion of the combination tag reader and tag.

18. The apparatus of claim 15 wherein two or more antenna near the holding area for each pill are coupled in series and to the tag reader portion of the combination tag reader and tag.

19. The apparatus of claim 15 wherein the tag is capable of operating as a near field device.

20. The apparatus of claim 15 wherein the tag portion of the combination tag reader and tag is capable of operating as a near field device.

21. A computer program product for tracking items, comprising instructions operable to cause a programmable processor to:
   receive a request on at least one combination tag reader and tag for the identity of an item associated with a tag;
   identify the item associated with the tag using the at least one combination tag reader and tag; and
   provide the identity of the item and tag through the at least one combination tag reader and tag.

22. The computer program product of claim 21 wherein the item is selected from a set of items including: drugs, medical devices, computer equipment, luxury items, and sports equipment.

23. The computer program product of claim 21 wherein the instructions that request further includes instructions that:
   pass the request for the identity of the item associated with the tag to a sequence of at least one or more combination tag reader and tags; and
   query through the tag reader portion of each of the one or more combination tag reader and tags for the identities of items associated with tags.

24. The computer program product of claim 21 wherein the instructions that request further include instructions that:
   cascade the request for the item associated with the tag to a daisy-chain sequence of at least one or more combination tag reader and tags wherein the cascade further includes instructions that,
   pass the request from the tag portion in each combination tag reader and tag through to the tag reader portion and onto a subsequent one or more combination tag reader and tags; and
   query the daisy-chain sequence of the one or more combination tag reader and tags for the identities of items associated with a tag.

25. The computer program product of claim 21 wherein the tag portion in the combination tag reader and tag is selected from a set of tag types including: a passive tag and an active tag.

26. An apparatus for tracking items, comprising:
- means for receiving a request on at least one combination tag reader and tag for the identity of an item associated with a tag;
- means for identifying the item associated with the tag using a tag reader portion of the at least one combination tag reader and tag; and
- means for providing the identity of the item and tag through a tag portion of the at least one combination tag reader and tag.

27. The apparatus of claim 26 wherein the at least one combination tag reader and tag means for receiving the request and further includes a means for receiving energy for both the tag reader portion and tag portion from a reader in a sequence of combination tag reader and tags.

28. A method of tracking an item, comprising:
- transmitting a request for one or more items through a sequence of one or more combination active tag and active tag reader;
- receiving the request and energy from at least one of the one or more combination active tag and tag reader on a first combination passive tag reader and tag that energizes both the tag portion and tag reader portion of the first passive combination tag reader and tag;
- passing the request and remaining energy from the first combination passive tag reader and tag to a daisy-chain sequence of one or more subsequent combination passive tag reader and tag powered by the remaining energy and each also capable of continuing to pass the request and subsequently remaining energy to other passive combination tag reader and tag.

29. The method of claim 28 further comprising:
- identifying an item associated with a tag using a combination passive tag reader and tag; and
- providing the identity of the item and tag through the combination passive tag reader and tag.

* * * * *

UNITED STATES PATENT AND TRADEMARK OFFICE
CERTIFICATE OF CORRECTION

| | |
|---|---|
| PATENT NO. | : 8,269,629 B2 |
| APPLICATION NO. | : 11/284494 |
| DATED | : September 18, 2012 |
| INVENTOR(S) | : Geoff Lyon et al. |

It is certified that error appears in the above-identified patent and that said Letters Patent is hereby corrected as shown below:

On the face page, in field (75), Inventors, in column 1, line 3, delete "Allpio" and insert -- Alipio --, therefor.

In column 11, line 66, in Claim 14, delete "lag" and insert -- tag --, therefor.

Signed and Sealed this
Nineteenth Day of March, 2013

Teresa Stanek Rea
*Acting Director of the United States Patent and Trademark Office*